United States Patent [19]

Hodgson et al.

[11] Patent Number: 4,798,906
[45] Date of Patent: Jan. 17, 1989

[54] PREPARATION OF ALKOXY HALIDES

[75] Inventors: Philip K. G. Hodgson, Walton-on-Thames; Nevin J. Stewart, Guildford, both of England

[73] Assignee: The British Petroleum Company p.l.c., London, England

[21] Appl. No.: 83,942

[22] Filed: Jul. 29, 1987

Related U.S. Application Data

[63] Continuation of Ser. No. 850,568, Apr. 11, 1986, abandoned.

[30] Foreign Application Priority Data

Apr. 16, 1985 [GB] United Kingdom ............... 85-09729

[51] Int. Cl.$^4$ ...................... C07C 41/03; C07C 41/22
[52] U.S. Cl. .................................... 568/614; 568/610; 568/649; 568/681
[58] Field of Search ............... 568/610, 614, 649, 696, 568/681

[56] References Cited

U.S. PATENT DOCUMENTS 3,830,851 8/1974 David et al. .
4,210,764 7/1980 Yang et al. .

FOREIGN PATENT DOCUMENTS 657080 2/1963 Canada .
467228 6/1937 United Kingdom .

OTHER PUBLICATIONS

Wagner et al, Synthetic Organic Chemistry, John Wiley & Sons, New York, 1953, p. 92.
Bartha, Tensile Detergents, vol. 10, No. 6, 1973, pp. 302–305 & English Translation.

Primary Examiner—Howard T. Mars
Attorney, Agent, or Firm—Morgan & Finnegan

[57] ABSTRACT

Alkyl-, aryl- or alkylaryl-alkoxy halides are prepared by reacting the corresponding alcohol, phenol or alkyl phenol with ethylene oxide and/or propylene oxide in the presence of an amine catalyst to form an alkoxy alcohol, and directly reacting the latter with a halogenating agent in the continuing presence of the amine catalyst.

Neutralization of the product and/or catalyst removal from the first stage is no longer necessary and reaction rates and yields are increased in the second stage.

8 Claims, No Drawings

PREPARATION OF ALKOXY HALIDES

This is a continuation of co-pending application Ser. No. 850,568, filed on Apr. 11, 1986, abandoned.

This invention relates to a process for the preparation of alkyl alkoxy, aryl alkoxy or alkylaryl alkoxy halides suitable for use as intermediates in the preparation of surfactants.

Numerous attempts have been made to develop surfactant compositions for use in enhanced oil recovery and the patent literature is replete with descriptions of formulations, see for example, U.S. Pat. No. 4,424,135, 4,159,037, 4,110,228, 4,066,124 and 4,018,278.

A useful summary of the art is given in Kirk-Othmer's Encyclopedia of Chemical Technology, Third Edition, Volume 17, pages 168–182. This indicates that most compositions contain (a) a main surfactant which is either a petroleum sulphonate or a synthetic hydrocarbyl sulphonate and (b) a co-surfactant which may be a simple alcohol, ethoxylated alcohol or a sulphated ethoxylated alcohol.

It has also been disclosed that alkyl and alkylaryl polyalkoxy alkylene sulphonates may be used as co-surfactants. These compounds are generally prepared by a three-stage process. In the first stage of a typical process an alcohol or alkyl phenol is condensed with an alkylene oxide in the presence of sodium or potassium hydroxide to form an alkoxylate. This is then halogenated by treatment with thionyl or sulphuryl chloride, usually in the absence of a catalyst. Finally the halide is converted to a sulphonate by reaction with sodium sulphite, again, usually in the absence of a catalyst.

The alkali catalyst is removed after the alkoxylation reaction since its presence is harmful to the stability of the product.

We have now discovered a process for the production of alkoxy halides from alcohols and phenols in which a single amine catalyst system is employed in both stages.

Thus according to the present invention there is provided a process for the production of an alkyl-, aryl- or alkylaryl-alkoxy halide which process comprises reacting an alcohol of formula $R^1$-OH, phenol or an alkyl phenol of formula

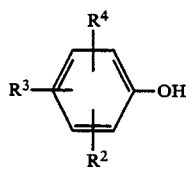

wherein
- $R^1$ is an alkyl group containing 1 to 24, preferably 8 to 20, carbon atoms,
- $R_2$ is an alkyl group containing 1 to 24, preferably 8 to 20, carbon atoms and $R^3$ and $R^4$ are hydrogen atoms, or
- $R^2$ and $R^3$ are both alkyl groups containing 1 to 12 carbon atoms and $R^4$ is a hydrogen atom, or
- $R^2$, $R^3$ and $R^4$ are each alkyl groups wherein the sum of the number of carbon atoms in the group is in the range 3 to 24;

with ethylene oxide and/or propylene oxide in the presence of an amine as catalyst to form an alkyl-, aryl- or alkylaryl-alkoxy alcohol containing 1 to 15, preferably 4 to 10, akoxy units per molecule, and directly reacting the alkoxylated reaction product with a halogenating agent in the continuing presence of the amine catalyst.

Suitable catalysts are of formula:

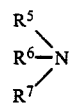

in which $R^5$, $R^6$ and $R^7$ independently of one another represent an alkyl, aryl or alkylaryl radical containing 1 to 18, preferably 1 to 6 carbon atoms, or a hydrogen atom, no more than two being hydrogen atoms, or any two of these radicals together with the nitrogen atom represent a heterocyclic ring.

Preferably the amine catalyst is a secondary amine. Suitable amines include ethanolamine, dibutylamine, triethylamine and piperidine.

Preferred halogenating agents are chlorinating agents such as thionyl chloride and sulphuryl chloride.

A pressure in the range of atmospheric to 7 bar may be employed for the alkoxylation stage.

Pressure is not a significant parameter for the halogenation stage and this reaction is therefore most conveniently carried out at ambient pressure.

Alkoxylation is suitably carried out at a temperature in the range 60° to 260° C., preferably 80° to 160° C., and halogenation is suitably effected at a temperature in the range 30° to 120° C., preferably in the range 75° to 85° C.

The molar ratio of alkoxy alcohol to halogenating agent in the halogenation stage is suitably in the range 1:1 to 1:5, preferably 1:1 to 1:5.

The quantity of catalyst employed is preferably in the range 0.1 to 10% by weight, preferably 0.2 to 1%, expressed as a percentage by weight of the alcohol, phenol or alkyl phenol.

The reactions may be effected in the presence or, preferably, the absence of a solvent. Suitably solvents include 1,2-dichloroethane, toluene and chloroform.

The process according to the present invention possesses the following advantages:

(1) A single catalyst can be used for both alkoxylation and halogenation reactions thus saving the cost of employing separate catalysts for each reaction;

(2) Neutralisation of the product and/or catalyst removal from the alkoxylation stage is no longer necessary.

(3) The catalyst is readily recoverable by extraction with water.

As a result of the reduced reaction time in the halogenation stage, the tendency of the polyoxyalkylene chain to cleave liberating 1,4-dioxan, noted by Robinson et al, J. Soc. Cosmet. Chem., 31, 329–337, is reduced. Thus both the yield and selectivity as indicated by the matching of the alkoxy distribution in the alcohol and the halide are improved and product contamination with unwanted by-product is reduced.

This invention is illustrated with reference to the following Examples. Example 1 is not in accordance with the invention and is provided for comparison.

EXAMPLE 1

Hexadecanol was treated with potassium hydroxide (0.3% w/w) at 100° C., under vacuum to remove water.

Ethoxylation was performed at 125° C. under 4 bar pressure to incorporate 4 moles ethylene oxide per mole alcohol.

The unrefined ethoxyalcohol $C_{16}H_{33}(OCH_2CH_2)_4OH$ (50 g, 0.12M) was heated with stirring at 80° C. with thionyl chloride (15.4 g, 0.129M).

$^{13}C$ NMR (Nuclear Magnetic Resonance) spectroscopy indicated 26% conversion to ethoxychloride after 2 hours and GLC (Gas Liquid Chromatography) indicated the production of 0.2 moles of 1,4-dioxan per mole ethoxyalcohol.

EXAMPLE 2

Hexadecanol was treated with di-n-butylamine (10% w/w) at 80° C. under a partial vacuum with nitrogen flush. Nitrogen sparging was continued at 80° C. over 0.5 hours at atmospheric pressure. Ethoxylation was performed at 80° C. under 4 bar pressure over 8 hours to incorporate 4 moles ethylene oxide per mole alcohol.

The unrefined ethoxyalcohol $C_{16}H_{33}(OCH_2CH_2)_4OH$ (53.8 g, 0.129M) was heated with stirring at 80° C. with thionyl chloride (16.5 g, 0.139M).

$^{13}C$ NMR spectroscopy indicated 92% conversion to ethoxychloride after 0.25 hours and GLC indicated the production of 0.006 moles of 1,4-dioxan per mole ethoxyalcohol.

In Example 1, the potassium hydroxide catalyst was effective for ethoxylation but not for chlorination. In Example 2, the amine catalyst was effective for both reactions.

It should be noted when comparing Examples 1 and 2 that the addition of a dual function catalyst resulted in a 28-fold increase in the chlorination rate and reduced dioxan production to 3% of its previous value.

We claim:

1. A process for the production of an alkyl-, aryl- or alkylaryl-alkoxy halide which process comprises reacting an alcohol of formula $R^1$—OH, phenol or an alkyl phenol of formula

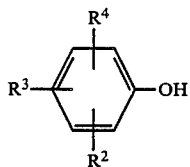

wherein $R^1$ is an alkyl group containing 1 to 24 carbon atoms, $R^2$ is an alkyl group containing 1 to 24 carbon atoms and $R^3$ and $R^4$ are hydrogen atoms, or $R^2$ and $R^3$ are both alkyl groups containing 1 to 12 carbon atoms and $R^4$ is a hydrogen atom, or $R^2$, $R^3$ and $R^4$ are each alkyl groups wherein the sum of the carbon number of the groups is in the range 3 to 24, with ethylene oxide and/or propylene oxide to form an alkyl- aryl- or alkylaryl-alkoxy alcohol containing 1 to 15 alkoxy units per molecule, wherein the alkoxylation reaction is carried out in the presence of a secondary amine as a catalyst and the alkoxyalcohol is directly reacted with a halogenating agent selected from the group consisting of thionyl chloride and sulphuryl chloride in the continuing presence of the amine catalyst.

2. A process according to claim 1 wherein the feedstock is an alcohol of formula $R^1$—OH, wherein $R^1$ is an alkyl group containing 8 to 20 carbon atoms and the alkoxyalcohol contains 4 to 10 alkoxy units per molecule.

3. A process according to claim 1 wherein alkoxylation is carried out at a pressure in the range atmospheric to 7 bar.

4. A process according to claim 1 wherein alkoxylation is carried out at a temperature in the range 60° to 260° C.

5. A process according to claim 1 wherein halogenation is carried out at a temperature in the range 30° to 120° C.

6. A process according to claim 1 wherein the molar ratio of the alkoxyalcohol to the halogenating agent is in the range 1:1 to 1:5.

7. A process according to claim 1 wherein the quantity of catalyst employed is in the range 0.1 to 10% by weight expressed as a percentage by weight of the alcohol, phenol or alkyl phenol.

8. A process according to claim 1 wherein the catalyst is of formula:

wherein $R^5$ and $R^6$ independently of one another represent an alkyl, aryl or alkylaryl containing 1–18 carbon atoms or together with the nitrogen atom represent a heterocyclic ring.

* * * * *